United States Patent [19]

Kiener et al.

[11] Patent Number: 5,702,930
[45] Date of Patent: Dec. 30, 1997

[54] **MICROBIOLOGICAL PROCESS FOR THE PREPARATION OF HETEROAROMATIC CARBOXYLIC ACIDS USING *ALCALIGENES FAECALIS***

[75] Inventors: Andreas Kiener, Visp; Jean-Paul Roduit, Grône; Rainer Glöckler, Visperterminen, all of Switzerland

[73] Assignee: Lonza, Ltd., Gampel/Valais, Switzerland

[21] Appl. No.: 659,362

[22] Filed: Jun. 6, 1996

[30] Foreign Application Priority Data

Jun. 7, 1995 [CH] Switzerland .................. 1664/95
Jun. 13, 1995 [CH] Switzerland .................. 1733/95

[51] Int. Cl.$^6$ ............... C12P 17/12; C12P 1/04; C12P 1/20
[52] U.S. Cl. ............ 435/122; 435/170; 435/252.1
[58] Field of Search ............... 435/121, 122, 435/252.1, 829, 170

[56] References Cited

U.S. PATENT DOCUMENTS 5,264,361  11/1993  Kiener ............... 435/252.1
5,270,203  12/1993  Kiener ............... 435/252.1

FOREIGN PATENT DOCUMENTS 0 187 680 A2  7/1986  European Pat. Off. .
0 444 640 A2  9/1991  European Pat. Off. .
0 447 004 A2  9/1991  European Pat. Off. .

OTHER PUBLICATIONS

Fischer et al. Berichte der Deutschen Chemischen Gesellschaft (1912) 45: 2456–2467.
Krieg, N. and Holt, J., Eds. Bergey's Manual of Systematic Bacteriology. vol. 1. Williams and Watkins: Baltimore. pp. 361–373, 1984.
Kobayashi et al., J. of Antibiotics, vol. 43, No. 10, (1990), pp. 1316–1320.
Mathew et al., Appln. Environmental Microbiology, vol. 54, No. 4 (1988) pp. 1030–1032.

Primary Examiner—Michael G. Wityshyn
Assistant Examiner—Susan Hanley
Attorney, Agent, or Firm—Fisher, Christen & Sabol

[57] ABSTRACT

A microbiological process for the preparation of a heteroaromatic carboxylic acid or one of its physiologically tolerated salts of the formulae I or II:

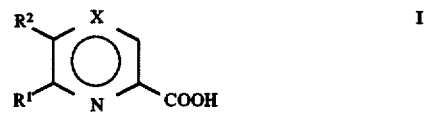

or

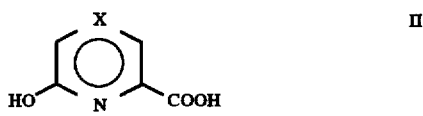

wherein $R_1$ and $R_2$ are identical or different and each denotes a hydrogen or halogen atom, and X denotes a nitrogen atom or CH—, from a heteroaromatic nitrile of the formulae III or IV, respectively:

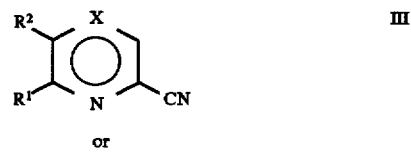

or

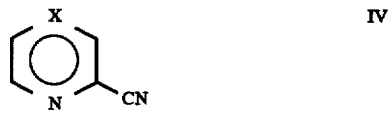

First, a microorganism, *Alcaligenes faecalis* (DSM 6335), is cultured in the presence of an inducer, 2-cyanopyridine, and a carbon source such as a dicarboxylic acid, a tricarboxylic acid or a carbohydrate. Substrate III or IV is then reacted with the cultured microorganism. The biotransformation is carried out under anaerobic conditions for compounds of the formula I, and under aerobic conditions for compounds of the formula II.

3 Claims, No Drawings

MICROBIOLOGICAL PROCESS FOR THE PREPARATION OF HETEROAROMATIC CARBOXYLIC ACIDS USING *ALCALIGENES FAECALIS*

BACKGROUND OF THE INVENTION

1. Field of the Invention

The invention relates to a novel microbiological process for the preparation of heteroaromatic carboxylic acids or their physiologically tolerated salts of the general formulae:

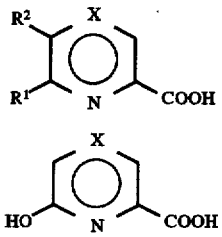

wherein $R^1$ and $R^2$ are identical or different and each denotes a hydrogen or halogen atom, and X denotes a nitrogen atom or —CH—.

Heteroaromatic carboxylic acids, such as, for example, 6-hydroxypicolinic acid, are important intermediate products for the preparation of pharmaceuticals, such as, for the preparation of 2-oxypyrimidine [*Berichte der Deutschen Chemischen Gesellschaft*, (1912), 45, pages 2456–2467] or for the preparation of herbicides (European Published Patent Application No. 0,447,004).

It is known in general that microorganisms containing nitrile hydratases and amidases or nitrilases convert nitriles into the corresponding acids. For example, European Published Patent Application No. 0,187,680 describes a microbiological process for the preparation of organic acids, such as, nicotinic acid using microorganisms of the genus Corynebacterium, Nocardia, Bacillus, Bacteridium, Micrococcus and Brevibacterium. It is obligatory to carry out this reaction in the presence of light energy. European Published Patent Application No. 0,444,640 discloses a microbiological process for the preparation of organic acids, such as, nicotinic acid using microorganisms of the genus Rhodococcus. It is obligatory to carry out this reaction in the presence of a lactam.

It is furthermore known that microorganisms of the species *Rhodococcus rhodochrous* J1 convert, for example, 2-cyanopyrazine to pyrazinecarboxylic acid [Kobayashi et al., J. of Antibiotics, Vol. 43, No. 10, (1990), pages 1316–1320]. However, these microorganisms are unable to convert 2-cyanopyridine into picolinic acid [Mathew et al., Appl. Environmental Microbiology, Vol. 54, No. 4, (1988), pages 1030–1032].

It is also known that 2-cyanopyridine-utilizing microorganisms of the genus Alcaligenes convert 2-cyanopyridine into 6-hydroxypicolinic acid (European Published Patent Application No. 0,504,818). It is a disadvantage of this process that the 6-hydroxypicolinic acid is formed only in moderate yield.

BROAD DESCRIPTION OF THE INVENTION

It is an object of the present invention to provide a more economic microbiological process for the preparation of heteroaromatic carboxylic acids or their physiologically tolerated salts, such as, pyrazinecarboxylic acid, picolinic acid or chromium picolinate using microorganisms of the genus Alcaligenes, wherein the formed carboxylic acids or their physiologically tolerated salts are formed in good yield. Other objects and advantages of the invention are set out herein or are obvious herefrom to one skilled in the art.

The objects and advantages of the invention are achieved by the process of the invention.

The invention involves a microbiological process for the preparation of heteroaromatic carboxylic acids or their physiologically tolerated salts of the general formulae:

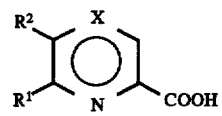

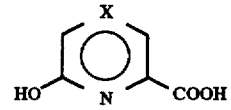

wherein $R^1$ and $R^2$ are identical or different and each denotes a hydrogen or halogen atom, and X denotes a nitrogen atom or —CH—. The invention process includes converting heteroaromatic nitriles of the general formulae:

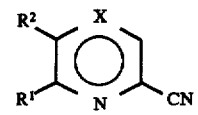

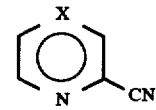

wherein $R^1$ and $R^2$ and X have the above-stated meanings, as substrate, using 2-cyanopyridine-utilizing microorganisms of the genus Alcaligenes which have been cultured before the biotransformation in the presence of a dicarboxylic acid, a tricarboxylic acid or a carbohydrate, into the corresponding carboxylic acid. The latter is converted where appropriate into physiologically tolerated salts.

DETAILED DESCRIPTION OF THE INVENTION

The process is carried out according to the invention in such a way that a heteroaromatic nitrile of the general formulae:

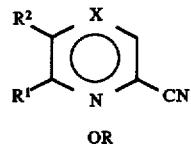

OR

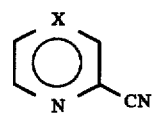

wherein X, $R^1$ and $R^2$ have the above-stated meanings, is converted as substrate, using 2-cyanopyridine-utilizing microorganisms of the genus Alcaligenes which have been cultured before the biotransformation in the presence of a dicarboxylic acid, a tricarboxylic acid or a carbohydrate, into heteroaromatic carboxylic acids according to Formula I or II. The heteroaromatic carboxylic acids are then converted where appropriate into physiologically tolerated salts. Physiologically tolerated salts of these carboxylic acids mean hereinafter, for example, chromium, calcium or ammonium salts.

Before the actual biotransformation, the microorganisms of the genus Alcaligenes used for the process are normally cultivated (cultured) and their effective enzymes expediently induced with 2-cyanopyridine. 2-Cyanopyridine can be used for culture and induction in a concentration of 0.1 to 20 percent by weight, preferably in a concentration of 0.1 to 1 percent by weight. A dicarboxylic acid means hereinafter fumaric acid, succinic acid, maleic acid, glutaric acid and malonic acid, and their salts and derivatives such as esters. A tricarboxylic acid means hereinafter citric acid and isocitric acid and their salts and derivatives such as esters. Salts and derivatives of these dicarboxylic acids and tricarboxylic acids which can be used are fumarate, malate, malonate, oxalacetate, citrate, aconitate, isocitrate, 2-oxoglutarate, succinate and succinyl-CoA. Fumarate, malonate or succinate is preferably used. Carbohydrates mean hereinafter monosaccharides such as glucose, disaccharides such as sucrose, trehalose or maltose, trisaccharides such as raftnose, and sugar alcohols such as glycerol. Glycerol is preferably used as the carbohydrate. The dicarboxylic acid, tricarboxylic acid or the carbohydrate is expediently used in a concentration of 0.1 to 20 percent by weight, preferably in a concentration of 0.5 to 5 percent by weight.

It is possible to use as culture medium the media customary among those skilled in the art, such as, the mineral salt medium of Kulla et al. [Arch. Microbiol., 135, 1–7, (1983)], low molarity phosphate buffer or as shown in Table 1. The mineral salt medium described in Table I is preferably used.

After the culture phase and before the actual addition of the substrate, either the microorganisms are harvested by conventional separation processes, or the substrate is added directly to the microorganisms.

The substrates used for the biotransformation, the heteroaromatic nitriles of the formulae III and IV, such as, 2-cyanopyridine, are purchasable compounds.

X in the general formulae I to IV denotes a nitrogen atom or —CH—, preferably —CH—. The radicals $R^1$ and $R^2$ are identical or different and denote hydrogen or halogen, such as, fluorine, chlorine, bromine or iodine. Possible substrates are, accordingly, 2-cyanopyridine, 6-chloro-2-cyanopyridine, 5,6-dichloro-2-cyanopyridine, 2-cyanopyrazine, 6-chloro-2-cyanopyrazine and 5-bromo-6-chloro-2-cyanopyrazine. 2-cyanopyridine, 2-cyanopyrazine or 6-chloro-2-cyanopyridine is expediently used as the substrate.

The substrate can be added all at once or continuously for the biotransformation. The substrate is expediently added in such a way that the substrate concentration in the medium does not exceed 20 percent by weight, preferably in such a way that the substrate concentration does not exceed 10 percent by weight.

The biotransformation, which is normally carried out with stationary cells, is expediently carried out using the 2-cyanopyridine-utilizing microorganisms of the species *Alcaligenes faecalis* which are disclosed in European Published Patent Application No. 0,504,818 and are designated DSM 6335, and using their functionally equivalent variants and mutants. These microorganisms were deposited on Jan. 3, 1991, (03/01/1991) at the Deutsche Sammlung von Mikroorganismen und Zellkulturen GmbH, Mascheroder Weg 1b, D-38124 Braunschweig, Germany, in accordance with the Budapest treaty.

"Functionally equivalent variants and mutants" mean microorganisms which have essentially the same properties and functions as the original microorganisms. Variants and mutants of this type can be formed adventitiously, for example by UV irradiation.

The same media can be used for the biotransformation as for the culturing of the microorganisms. The biotransformation can also take place in the presence or absence of the dicarboxylic acids, tricarboxylic acids or carbohydrates described above.

The pH is expediently in a range from 4 to 10, preferably in a range from 5 to 9. The biotransformation can be carried out at a temperature from 10° to 50° C., preferably at a temperature from 20° to 40° C.

After a usual conversion time of 6 to 100 hours, the appropriate carboxylic acids according to formula I or II can then be obtained by customary working up methods, such as, by acidification. The carboxylic acids can also be isolated in the form of salts, such as, ammonium or chromium salt.

If the prepared heteroaromatic carboxylic acids are heteroaromatic carboxylic acids hydroxylated in position 6 (general formula II), the biotransformation is expediently carried out under aerobic conditions. If, however, a non-hydroxylated heteroaromatic carboxylic acid, such as, picolinic acid is prepared, the biotransformation is expediently carried out under anaerobic conditions.

EXAMPLE 1

Preparation of 6-hydroxypicolinic Acid

The conditions chosen for the preparation of 6-hydroxypicolinic acid using the strain Alcaligenes faecalis DSM 6335 were as follows. A 7.5 l fermenter with an operating volume of 5 l was used. *Alcaligenes faecalis* DSM 6335 was cultured in a mineral salt medium (Table 1) with sodium fumarate as the sole source of carbon and energy, and 2-cyanopyridine as inducer at 30° C., 600 rpm and a pH of 7.0. The aeration rate was about 3 l/min during this operation. Addition of the sodium fumarate took place under $pO_2$ control when the $pO_2$ was >30 percent. A 20 percent strength stock solution of sodium fumarate to which 0.5 percent, 2-cyanopyridine was added was used. The cells were cultured until the optical density, measured at 650 nm ($OD_{650}$), was 16 over the course of 23 hours before the biotransformation was started. For the growth phase, about 160 g of sodium fumarate in the form of a 20 percent strength solution (about 800 ml) was used.

No source of carbon and energy was added during the aerobic biotransformation of 2-cyanopyridine to 6-hydroxypicolinic acid. The biotransformation took place with stationary cells.

The addition of the 2-cyanopyridine took place by means of a pump with limitation. The pump rate was monitored "online" by means of HPLC. The concentration of the intermediate picolinic acid, whose rate of formation is about 2.5 times greater than the rate of conversion of picolinic acid into 6 -hydroxypicolinic acid (10 g/l·h to 4 g/l·h), was limited to values <2 g/l, since otherwise the conversion of picolinic acid into 6-hydroxypicolinic acid was inhibited.

Since 2-cyanopyridine is a solid at room temperature, it was necessary to heat the reservoir containing 2-cyanopyridine to 50° C., making it possible to add 2-cyanopyridine in liquid form. It was possible with this process to prepare 75 g/l 6-hydroxypicolinic acid within 31 hours. The intermediate picolinic acid was no longer detectable at the end of the biotransformation.

To isolate the 6-hydroxypicolinic acid, the cells were removed by filtration. The cell-free solution was then heated to 60° C. and acidified with concentrated sulfuric acid to a pH of 2 to 2.5. At this pH, the 6-hydroxypicolinic acid was precipitated from the solution.

It was then slowly cooled, with stirring, to 4° C. and filtered, and the residue was washed with demineralized water and dried (100 mbar, 55° C.). About 2 g/l 6-hydroxypicolinic acid remained in the mother liquor from this washing. The yield was 87 percent based on 2-cyanopyridine used.

TABLE 1

| Composition | Concentration, (g/l) |
|---|---|
| Disodium fumarate | 10 |
| Yeast extract | 1 |
| $MgCl_2.6H_2O$ | 0.8 |
| $Na_2SO_4$ | 0.25 |
| $(NH_4)_2SO_4$ | 1.0 |
| $NH_4Cl$ | 2.33 |
| NaCl | 0.2 |
| $CaCl_2.2H_2O$ | 0.16 |
| $MnSO_4$ | $1.8 \cdot 10^{-2}$ |
| $H_3BO_3$ | $3 \cdot 10^{-2}$ |
| $NiCl_2$ | $2 \cdot 10^{-3}$ |
| $NaMoO_4$ | $3 \cdot 10^{-3}$ |
| $FeSO_4.7H_2O$ | 0.3 |
| $Na_2EDTA.2H_2O$ | 0.75 |
| 2-Cyanopyridine | 1 |
| $KH_2PO_4$ | 0.4 |
| $Na_2HPO_4$ | 0.96 |

EXAMPLE 2

Preparation of Picolinic Acid

The biomass was cultured as described in Example 1. The formation of picolinic acid took place under strictly anaerobic conditions. A 500 ml glass bottle with rubber septum charged with 400 ml of biomass of $OD_{650}=20$ was used for the biotransformation. Incubation took place at 30° C. Before the biotransformation was started, the mixture was made anaerobic with pure nitrogen. For this purpose, nitrogen (50 mbar gauge pressure) was passed through a needle into the stirred mixture for about 30 minutes in order to drive out the oxygen quantitatively. In order to prevent oxygen from entering during the biotransformation or on addition of the 2-cyanopyridine, the gas introduction was maintained during the biotransformation (about 10 mbar gauge pressure). 2-cyanopyridine was added in 12 steps each of 10 g/l, in each case after one hour had elapsed. The addition can, however, also take place continuously. HPLC was used to check whether 2-cyanopyridine had been completely converted into picolinic acid before adding another portion. During the biotransformation there was no detectable formation of picolinamide. It was possible with this process to prepare about 150 g/l picolinic acid within 26 hours. 6-Hydroxypicolinic acid was not formed during this.

For isolation, the cell-free picolinic acid solution was precipitated with $CaCl_2/H_2SO_4$. For this purpose, the cell-free picolinic acid solution from Example 2 was diluted 3-fold and, while stirring, 0.5 equivalent of $CaCl_2$ per equivalent of picolinic acid was added after the cell-free fermentation solution had been heated to 90° C. The resulting calcium/picolinic acid complex precipitated immediately. The resulting complex was cooled to 4° C. with stirring, filtered off on a glass flit (porosity 3) and washed with demineralized water. The filter cake was suspended in demineralized water and acidified to a pH of 2.5 with concentrated sulfuric acid. During this operation, the picolinic acid was dissolved out of the complex and, at the same time, insoluble calcium sulfate was formed. Since the free picolinic acid is very soluble in water it was possible to remove calcium sulfate by filtration. The picolinic acid solution was evaporated to dryness and analyzed. The crude yield was about 70 percent with a purity of 86 percent by titration. The water content was 0.7 percent measured by the Karl-Fischer method.

EXAMPLE 3

Preparation of Chromium(III) Picolinate

Aqueous chromium trichloride hexahydrate solution (23.95 g, 0.09 mol of Cr in 63 ml of water/was added dropwise over a period of 3.5 hours to an ammonium picolinate solution (271.4 g; 0.325 mol; 16.8%), pH 7.1, 73° C. in a 500 ml flask. The resulting violet solution was stirred for a further 1 hour and then slowly cooled to 3° C. After the red solid which had formed had settled out, the upper blue phase was decanted off. The solid was suspended in 100 ml of water for 30 min., and decantation was repeated. After a second suspension in 50 ml of water (30 min.), the solid was filtered off with suction and dried at 50° C. in vacuo. 33.64 g of dark red crystals was obtained (90 percent yield).

EXAMPLE 4

Culturing of *Alcaligenes faecalis* DSM 6335 with Various Sources of Carbon 300 ml conical flasks containing 100 ml of A+N medium (Table 1 without disodium fumarate) were used for culturing Alcaligenes faecalis (DSM 6335), and in addition, 2 $gl^{-1}$ 2-cyanopyridine and 10 $gl^{-1}$ of one of the following sources of carbon were added to the medium:

disodium fumarate
glycerol
disodium malonate
disodium succinate

Incubation took place in a shaker at 30° C. After growth for 16 hours, the cells were spun down and resuspended in fresh A+N medium (without source of carbon) containing 10 $gl^{-1}$ 2-cyanopyridine. The optical density of the cell suspension, measured at 650 nm ($OD_{650}$), was 10. The cell suspensions (total volume 10 to 20 ml) were then incubated again at 30° C. The formation of 6-hydroxypicolinic acid was followed by spectrophotometry, measuring the absorption of the cell-free solution at 308 nm. The following average productivities were determined for the formation of 6-hydroxypicolinic acid:

| Carbon | Productivity (in $gl^{-1}h^{-1}$) |
|---|---|
| Disodium fumarate | 2.4 |
| Glycerol | 2.0 |
| Disodium malonate | 4.2 |
| Disodium succinate | 0.14 |

EXAMPLE 5

Preparation of 6-hydroxypyrazinecarboxylic Acid

*Alcaligenes faecalis* (DSM 6335) was cultured as in Example 4 with fumaric acid as the source of carbon. The washed cells were resuspended in A+N medium containing 10 $gl^{-1}$ 2-cyanopyrazine ($OD_{650}=10$) and incubated at 30° C. The formation of 6-hydroxypyrazinecarboxylic acid was followed by spectrophotometry, measuring the absorption of the cell-free solution at 320 nm. It was possible to determine the decrease in the concentration of 2-cyanopyrazine (substrate) by measuring the absorption at 270 nm. The amount of 2-cyanopyrazine used had been converted into 6-hydroxypyrazinecarboxylic acid after 7 hours.

EXAMPLE 6

Preparation of 6-chloropicolinic Acid and Pyrazinecarboxylic Acid

*Alcaligenes faecalis* (DSM 6335) was cultured as in Example 4 with fumaric acid as source of carbon. The washed cells were resuspended in A+N medium in glass vessels ($OD_{650}$=10) which could be closed with rubber stoppers, and nitrogen was introduced through needles in order to remove dissolved oxygen. Then, 2-cyanopyrazine or 6-chloro-2-cyanopyridine was added as substrate to the cell suspensions, until the final concentration was 10 $gl^{-1}$, and incubated at 30° C. After 3 hours, the starting substances had been converted quantitatively into the corresponding acids [detection by thin-layer chromatography; silica gel 60 with fluorescence indicator, mobile phase: chloroform 30/ethanol 55/$NH_4OH$ (25%) 10/$H_2O$ 5].

What is claimed is:

1. A microbiological process for the preparation of a heteroaromatic carboxylic acid or one of its physiologically tolerated salts of the formulae I or II:

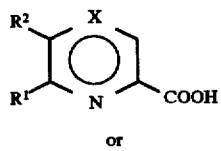
I or

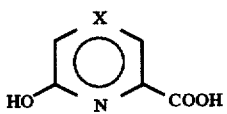
II wherein $R_1$ and $R_2$ are identical or different and each denotes a hydrogen or halogen atom, and X denotes a nitrogen atom or CH—, comprising converting a heteroaromatic nitrile of the formulae III or IV:

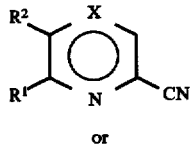
III or

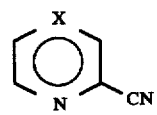
IV as substrate, wherein $R_1$ and $R_2$ have the above stated meanings, comprising the steps of:

a) culturing a microorganism having all the identifying characteristics of *Alcaligenes faecalis* (DSM 6335) in the presence of the inducer, 2-cyanopyridine, and a carbon source selected from the group consisting of a dicarboxylic acid, a tricarboxylic acid and a carbohydrate;

b) reacting the substrate III or IV with the cultured microorganism, wherein the biotransformation is carried out under anaerobic conditions when compounds of the formula I are desired, and under aerobic conditions when compounds of the formula II are desired;

c) recovering the carboxylic acid I or II; and d) converting the carboxylic acid I or II, where appropriate, into the corresponding physiologically tolerated salt.

2. The process according to claim 1, wherein the biotransformation is carried out at a pH of 4 to 10 and a temperature of 10° to 50° C.

3. A microbiological process for the preparation of picolinic acid or one of its physiologically tolerated salts from 2-cyanopyridine, comprising the steps of:

a) culturing a microorganism having all the identifying characteristics of *Alcaligenes faecalis* (DSM 6335) in the presence of a carbon source selected from the group consisting of a dicarboxylic acid, a tricarboxylic acid and a carbohydrate;

b) reacting 2-cyanopyridine with the cultured microorganism, wherein the biotransformation is carried out under anaerobic conditions;

c) recovering picolinic acid; and d) converting picolinic acid, where appropriate, into the corresponding physiologically tolerated salt.

* * * * *